(12) United States Patent
Patel

(10) Patent No.: US 7,255,439 B1
(45) Date of Patent: Aug. 14, 2007

(54) EYE DIVERSION ASSEMBLY AND METHOD

(76) Inventor: Nikul Patel, 808 Leadership Ct., Toms River, NJ (US) 08755

(*) Notice: Subject to any disclaimer, the term of this patent is extended or adjusted under 35 U.S.C. 154(b) by 191 days.

(21) Appl. No.: 11/232,144

(22) Filed: Sep. 22, 2005

(51) Int. Cl.
*A61B 3/00* (2006.01)

(52) U.S. Cl. .............. 351/203; 351/246; 351/200; 351/245

(58) Field of Classification Search .............. 351/203, 351/200, 244, 245, 246, 217, 225, 234
See application file for complete search history.

(56) References Cited

U.S. PATENT DOCUMENTS

| | | | |
|---|---|---|---|
| 1,464,075 A * | 8/1923 | Hull | ............................. 351/203 |
| 4,074,153 A | 2/1978 | Baker et al. | |
| 4,215,330 A | 7/1980 | Hartman | |
| 5,842,902 A | 12/1998 | Liff | |
| 5,880,811 A * | 3/1999 | Parisi | ........................... 351/203 |
| 6,042,231 A | 3/2000 | Fateh | |
| 6,139,149 A | 10/2000 | Shafer et al. | |
| D443,657 S | 6/2001 | Chesler | |

* cited by examiner

*Primary Examiner*—Ricky Mack
*Assistant Examiner*—Tuyen Tra

(57) ABSTRACT

An eye diversion assembly includes a base that has a top wall, a bottom wall and a perimeter wall. A pair of supports extends upwardly from the top wall. An axle is rotatably coupled to and extends between the supports. The axle extends through a plurality of panels. The axle extends through a central area of each of the panels. At least one of the panels is fixedly coupled to the axle and at least one of the panels is rotatably coupled to the axle. Each of a plurality of magnets is attached to one of the panels. A drive assembly mounted in the base is mechanically coupled to the axle. The drive assembly is configured to selectively rotate the axle. A power supply is electrically coupled to the drive assembly. A person's eyes are diverted toward the panels when the drive assembly is turned on.

9 Claims, 4 Drawing Sheets

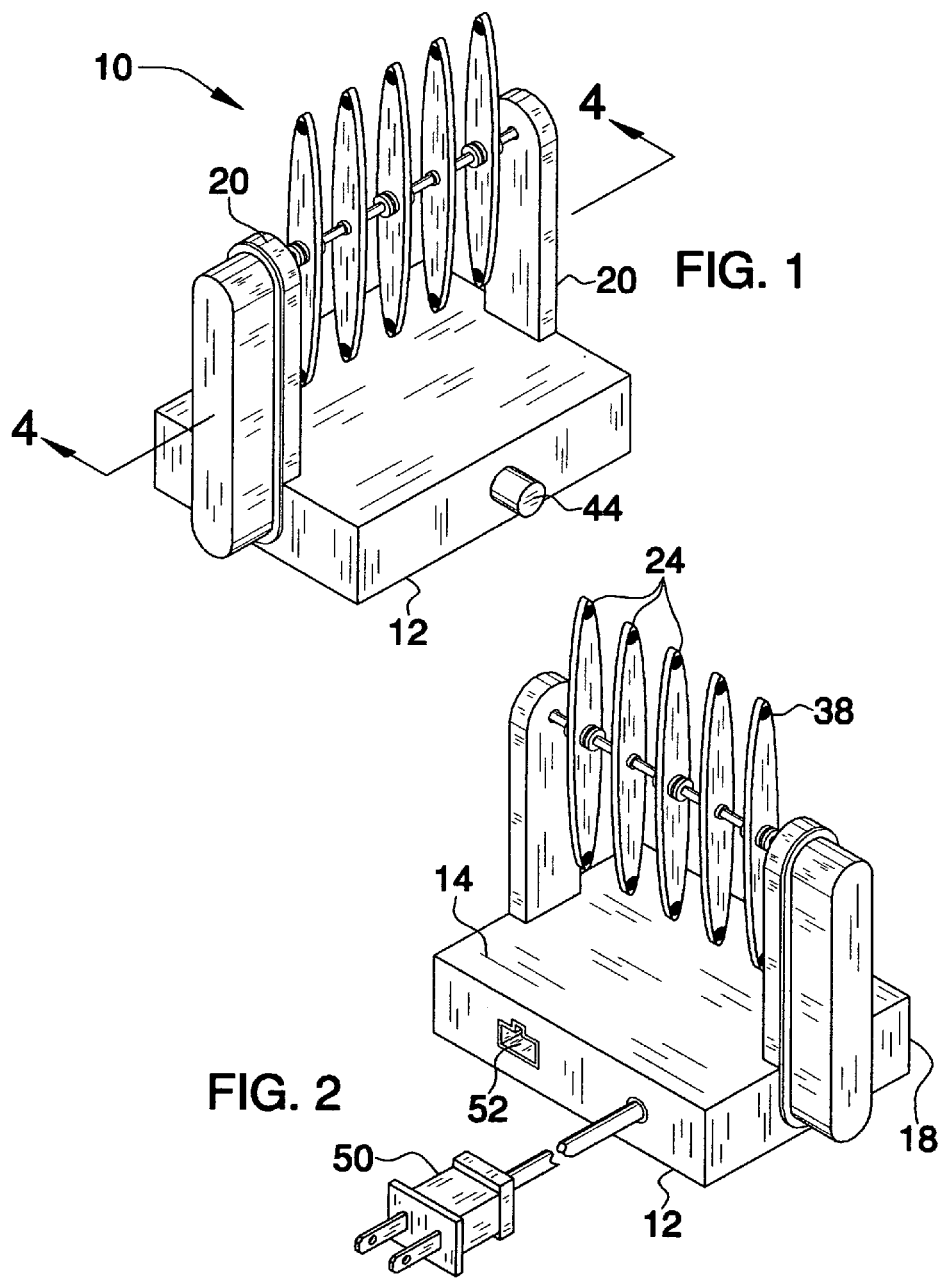

EYE DIVERSION ASSEMBLY AND METHOD

BACKGROUND OF THE INVENTION

1. Field of the Invention

The present invention relates to eyestrain relieving devices and more particularly pertains to a new eye strain relieving device for diverting a person's eyes from a computer screen so that the person is forced to refocus their eyes and thereby prevent eyestrain.

2. Description of the Prior Art

The use of eyestrain relieving devices is known in the prior art. U.S. Pat. No. 6,042,231 describes a system for aiding a person in performing eye exercises with the goal of reducing eyestrain. device/system for . . . Another type of eyestrain relieving device is U.S. Pat. No. 6,139,149 having a suspending, three dimensional structure that may be focused on to relieve eyestrain. Other devices that are related to the present invention include those which use magnets for inducing propulsion of other objects. Such devices are found in U.S. Pat. No. 4,215,330 and U.S. Pat. No. 4,074,153.

While these devices fulfill their respective, particular objectives and requirements, the need remains for a method that includes a plurality of spinning panels which provide multiple variations of depth perspective so that a person's eyes are diverted toward the panels and the focusing of the eyes is encouraged by the varying depth perspective. Further, the method should include an assembly that is connectable to a computer work station to allow the work station to control the actuation of the assembly.

SUMMARY OF THE INVENTION

The present invention meets the needs presented above by generally comprising a base that has a top wall, a bottom wall and a perimeter wall that is attached to and extends between the top and bottom walls. A pair of supports is attached to and extends upwardly from the top wall. The supports are spaced from each other. An axle is rotatably coupled to and extends between the supports. The axle extends through a plurality of panels. The axle extends through a central area of each of the panels. At least one of the panels is fixedly coupled to the axle and at least one of the panels is rotatably coupled to the axle. Each of a plurality of magnets is attached to one of the panels. A drive assembly mounted in the base is mechanically coupled to the axle. The drive assembly is configured to selectively rotate the axle. A power supply is electrically coupled to the drive assembly. A person's eyes are diverted toward the panels when the drive assembly is turned on.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front perspective view of a eye diversion assembly and method according to the present invention.

FIG. 2 is a rear perspective view of the present invention.

DESCRIPTION OF THE PREFERRED EMBODIMENT

Figure 3:
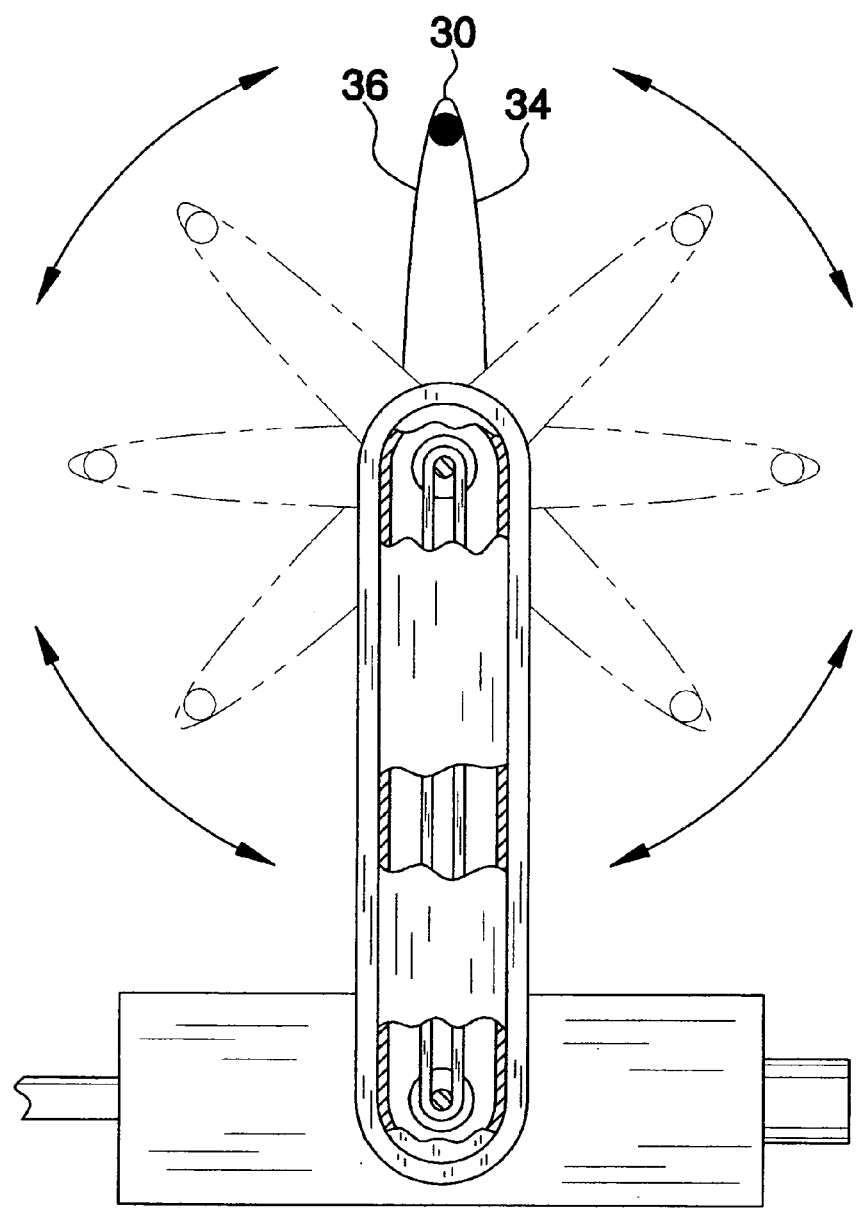
FIG. 3 is an end view of the present invention.
Figure 4:
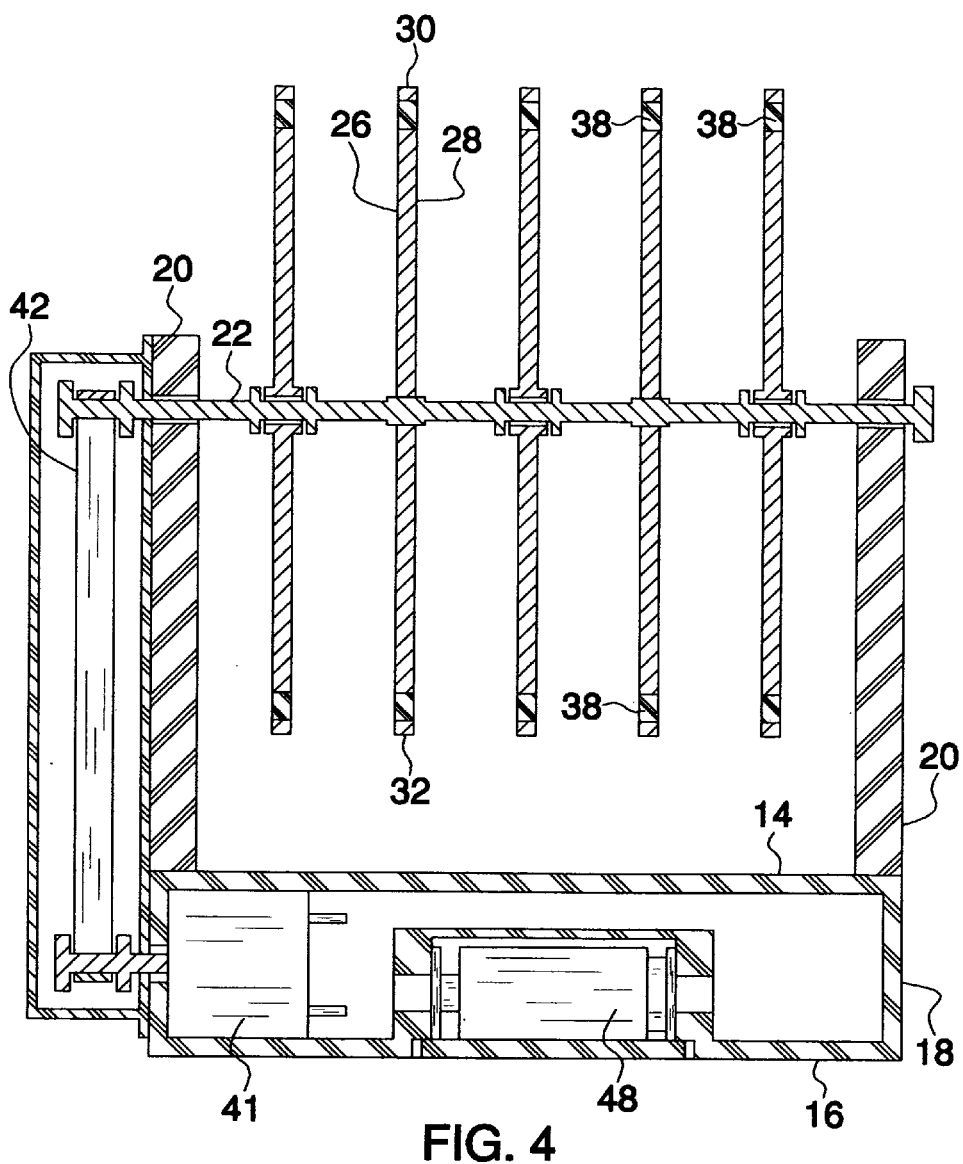
FIG. 4 is a cross-sectional view taken along line 4-4 of FIG. 1 of the present invention.
Figure 5:
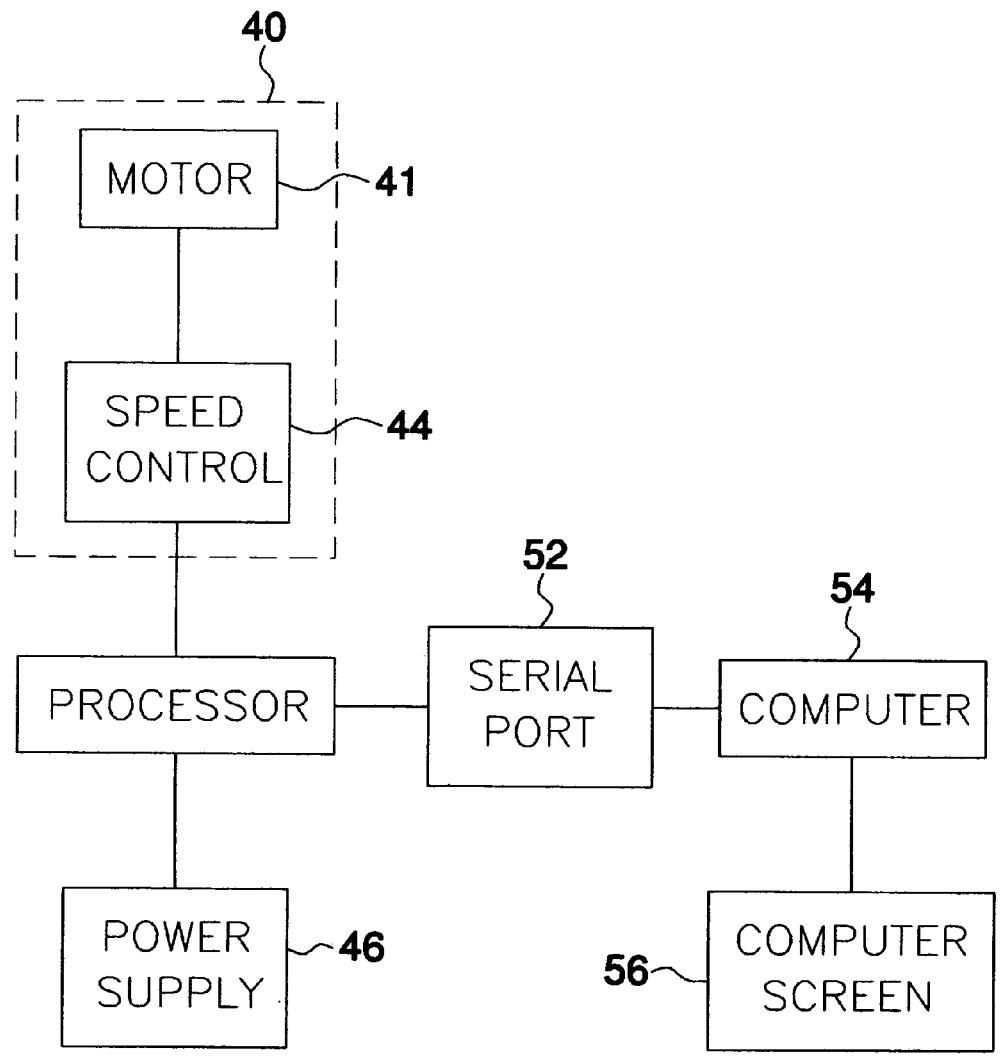
FIG. 5 is a schematic view of the present invention.

With reference now to the drawings, and in particular to FIGS. 1 through 5 thereof, a new eyestrain relieving device embodying the principles and concepts of the present invention and generally designated by the reference numeral 10 will be described.

As best illustrated in FIGS. 1 through 5, the eye diversion assembly and method 10 generally comprises a base 12 that has a top wall 14, a bottom wall 16 and a perimeter wall 18 that is attached to and extends between the top 14 and bottom 16 walls. A pair of supports 20 is attached to and extends upwardly from the top wall 14. The supports 20 are spaced from each other. An axle 22 is rotatably coupled to and extending between the supports 20.

A plurality of panels 24 is provided. Each of the panels 24 has a first side 26, a second side 28, a first end edge 30, a second end edge 32, a first lateral edge 34 and a second lateral edge 36. The first 34 and second 36 lateral edges are elongated with respect to the first 30 and second 32 end edges, which are preferably arcuate. The axle 22 extends through each of the first 26 and second 28 sides of the panels 24. The panels 24 are positioned between ¼ inch and 1 inch away from each other. The axle 22 extends through a central area of each of the panels 24. At least one of the panels 24 is fixedly coupled to the axle 22 and at least one of the panels 24 is rotatably coupled to the axle 22. Each of the rotatably coupled panels 24 is positioned adjacent to one of the fixedly coupled panels 24. It is preferred that the plurality of panels 24 is five panels wherein two of the panels are fixedly coupled to the axle 22 and the remaining three panels are rotatably coupled to the axle 22. The rotatably coupled panels 24 are positioned on either side of the fixedly coupled panels 24.

A plurality of magnets 38 is provided. Each of the magnets 38 is attached to one of the panels 24 so that each of the panels 24 has a pair of magnets 38 attached thereto. Each of the magnets 38 of the pairs of magnets is positioned adjacent to a respective one of the first 30 or second 32 end edges. The magnets 38 are positioned so that their magnetic fields interact with each other and may be arranged selectively with respect to north or south poles to encourage or discourage repelling magnetic fields.

A drive assembly 40 is mounted in the base 12 and includes a motor 41 mechanically coupled to the axle 22 by a drive belt 42. The drive assembly 40 is configured to selectively rotate the axle 22. The drive assembly 40 includes a speed control 44 for selectively determining a rotational speed of the axle 22. The speed control 44 may also be used for turning the drive assembly 40 on or off. A power supply 46 is electrically coupled to the drive assembly 40. The power supply 46 may include a battery 48 removably positioned in the base 12 and also includes an electrical cord 50 so that a user may choose between battery or electrical outlet power.

A serial port 52, or any other conventional data transfer port such as a universal serial bus, is electrically coupled to the drive assembly 40. The serial port 52 may be used for controlling the drive assembly 40 via a personal computer 54. The personal computer 54 is operationally coupled to the serial port 52 and is configured to intermittently turn on the drive assembly. The personal computer 54 may be programmed to rotate the axle 22 at selected intervals, such as between 15 minutes and 60 minutes. The user of the assembly 10 would typically be viewing a computer screen 56 that is operationally coupled to the personal computer 54. The eyes of the user of the assembly 10 are diverted away from the computer screen 56 and toward the panels 24 when the drive assembly 40 is turned on. In this manner, eyestrain will be reduced as the user focuses their eyes on the panels 24. The magnets 38 on the fixed panels 24 drag or repel the magnets 38 on the adjacent, non-fixed panels 24 so that the panels 24 rotate separately and erratically with respect to each other.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of relieving eyestrain comprising the steps of:
   providing a base having a top wall, a bottom wall and a perimeter wall being attached to and extending between said top and bottom walls, a pair of supports being attached to and extending upwardly from said top wall, said supports being spaced from each other, an axle being rotatably coupled to and extending between said supports;
   providing a plurality of panels, said axle extending through each of said panels, said axle extending through a central area of each of said panels, at least one of said panels being fixedly coupled to said axle and at least one of said panels being rotatably coupled to said axle;
   providing a plurality of magnets, each of said magnets being attached to one of said panels;
   providing a drive assembly mounted in said base and being mechanically coupled to said axle, said drive assembly being configured to selectively rotate said axle;
   providing a power supply being electrically coupled to said drive assembly; and
   diverting a person's eyes toward said panels when said drive assembly is turned on.

2. The method according to claim 1, wherein each of said panels has a first side, a second side, a first end edge, a second end edge, a first lateral edge and a second lateral edge, said first and second lateral edges being elongated with respect to said first and second end edges.

3. The method according to claim 2, wherein each of said panels has a pair of magnets attached thereto.

4. The method according to claim 3, wherein each of said magnets of said pairs of magnets being positioned adjacent to a respective one of said first or second end edges.

5. The method according to claim 1, wherein said axle extends through a central area of each of said panels.

6. The method according to claim 1, wherein each of said rotatably coupled panels is positioned adjacent to one of said fixedly coupled panels.

7. The method according to claim 1, wherein said drive assembly includes a speed control for selectively determining a rotational speed of said axle.

8. The method according to claim 1, further including the steps of:
   providing a serial port electrically coupled to said drive assembly;
   providing a personal computer being operationally coupled to said serial port, said personal computer being and being configured to intermittently turn on said drive assembly;
   providing a computer screen being operationally coupled to said personal computer, wherein the person's eyes are diverted away from said computer screen when said drive assembly is turned on.

9. A method of relieving eyestrain comprising the steps of:
   providing a base having a top wall, a bottom wall and a perimeter wall being attached to and extending between said top and bottom walls, a pair of supports being attached to and extending upwardly from said top wall, said supports being spaced from each other, an axle being rotatably coupled to and extending between said supports;
   providing a plurality of panels, each of said panels having a first side, a second side, a first end edge, a second end edge, a first lateral edge and a second lateral edge, said first and second lateral edges being elongated with respect to said first and second end edges, said axle extending through each of said panels, said axle extending through a central area of each of said panels, at least one of said panels being fixedly coupled to said axle and at least one of said panels being rotatably coupled to said axle, each of said rotatably coupled panels being positioned adjacent to one of said fixedly coupled panels;
   providing a plurality of magnets, each of said magnets being attached to one of said panels such that each of said panels has a pair of magnets attached thereto, each of said magnets of said pairs of magnets being positioned adjacent to a respective one of said first or second end edges;
   providing a drive assembly mounted in said base and being mechanically coupled to said axle, said drive assembly being configured to selectively rotate said axle, said drive assembly including a speed control for selectively determining a rotational speed of said axle;
   providing a power supply being electrically coupled to said drive assembly;
   providing a serial port electrically coupled to said drive assembly;
   providing a personal computer being operationally coupled to said serial port and being configured to intermittently turn on said drive assembly;
   providing a computer screen being operationally coupled to said personal computer; and
   diverting a person's eyes away from said computer screen and toward said panels when said drive assembly is turned on.

* * * * *